United States Patent
Lawrence et al.

(10) Patent No.: US 11,749,384 B2
(45) Date of Patent: Sep. 5, 2023

(54) CODE POINT RESOLUTION USING NATURAL LANGUAGE PROCESSING AND METATHESAURUS

(71) Applicant: Merative US L.P., Ann Arbor, MI (US)

(72) Inventors: Nicholas Todd Lawrence, Rochester, MN (US); Fernando Jose Suarez Saiz, Toronto (CA); Corey Sanders, Hilliard, OH (US); Robert Louis Nielsen, Chapel Hill, NC (US)

(*) Notice: Subject to any disclaimer, the term of this patent is extended or adjusted under 35 U.S.C. 154(b) by 167 days.

(21) Appl. No.: 17/161,828

(22) Filed: Jan. 29, 2021

(65) Prior Publication Data
US 2022/0246253 A1 Aug. 4, 2022

(51) Int. Cl.
| | |
|---|---|
| *G16H 10/00* | (2018.01) |
| *G06F 40/205* | (2020.01) |
| *G16H 70/00* | (2018.01) |
| *G06F 40/174* | (2020.01) |
| *G06F 40/55* | (2020.01) |
| *G06F 40/247* | (2020.01) |

(52) U.S. Cl.
CPC .......... *G16H 10/00* (2018.01); *G06F 40/174* (2020.01); *G06F 40/205* (2020.01); *G06F 40/247* (2020.01); *G06F 40/55* (2020.01); *G16H 70/00* (2018.01)

(58) Field of Classification Search
CPC ................................ G16H 10/00; G16H 70/00
See application file for complete search history.

(56) References Cited

U.S. PATENT DOCUMENTS

| | | | |
|---|---|---|---|
| 9,946,991 B2 | 4/2018 | Mills | |
| 10,275,424 B2 | 4/2019 | Friedman | |
| 10,395,772 B1 | 8/2019 | Lucas et al. | |
| 10,423,633 B2 | 9/2019 | Mirhaji | |
| 10,614,196 B2 | 4/2020 | Maitra et al. | |
| 10,740,678 B2 | 8/2020 | Ho et al. | |
| 2006/0052945 A1* | 3/2006 | Rabinowitz | G16H 50/70 702/20 |
| 2009/0024615 A1* | 1/2009 | Pedro | G06F 16/367 707/999.005 |
| 2011/0246234 A1* | 10/2011 | Irwin | G06F 16/215 705/3 |

(Continued)

OTHER PUBLICATIONS

Scheurwegs, E., "Data Integration for Clinical Coding Algorithms", 160 pages, 2017.

(Continued)

*Primary Examiner* — Jesse S Pullias
(74) *Attorney, Agent, or Firm* — Stephen J. Walder, Jr.

(57) ABSTRACT

A system and related method exchange medical information with a medical management system. The method comprises receiving, using a processor of a code point resolver, from the medical management system, medical text via a network interface. A code point is a single standardized medical terminology code (SMTC) that corresponds to a medical concept contained within the medical text. The method further applies rule-based logic to process the medical text to form a localized mapping of a text portion of the medical text to a plurality of candidate SMTCs (CSMTCs) that are related to at least one metathesaurus concept entity (MCE) in a metathesaurus, and to determines the code point from the CSMTCs. The method transmits, via the network interface, to the medical management system, the code point.

20 Claims, 10 Drawing Sheets

(56) References Cited

U.S. PATENT DOCUMENTS

| | | | | |
|---|---|---|---|---|
| 2013/0066903 A1* | 3/2013 | Tymoshenko | ......... | G06F 40/30 707/769 |
| 2014/0122117 A1* | 5/2014 | Masarie, Jr. | ........... | G16H 70/20 705/3 |
| 2015/0356270 A1* | 12/2015 | Devarakonda | ......... | G16H 50/70 705/3 |
| 2018/0349555 A1* | 12/2018 | Devarakonda | ......... | G16H 50/20 |

OTHER PUBLICATIONS

BioNLP 2014, Workshop on Biomedical Natural Language Processing, Proceedings of the Workshop, Baltimore, Maryland, USA, 155 pages, Jun. 27-28, 2014.

Aronson, A. et al., "An Overview of MetaMap: Historical Perspective and Recent Advances", Journal of the American Medical Informatics Association, 9 pages, May 2010.

Authors et al.: Disclosed Anonymously, A Back-Off Methods for Identifying Relevant Content for ICD-10-CM Codes, ip.com No. IPCOM000245414D, Mar. 8, 2016, 4 pages.

Authors et al.: Disclosed Anonymously, Identification of Relevant Content for ICD-10 Coding in Electronic Health Records, IP.com No. IPCOM000245413D, Mar. 8, 2016.

Authors et al.: Disclosed Anonymously, Axis-Based Natural Language Processing Supported ICD10-PCS Computer Assisted Coding Workflow, IP.com No. IPCOM000245412D, Mar. 8, 2016, 9 pages.

Mell, P. et al., "The NIST Definition of Cloud Computing", Recommendations of the National Institute of Standards and Technology, NIST Special Publication 800-145, 7 pages, Sep. 2011.

* cited by examiner

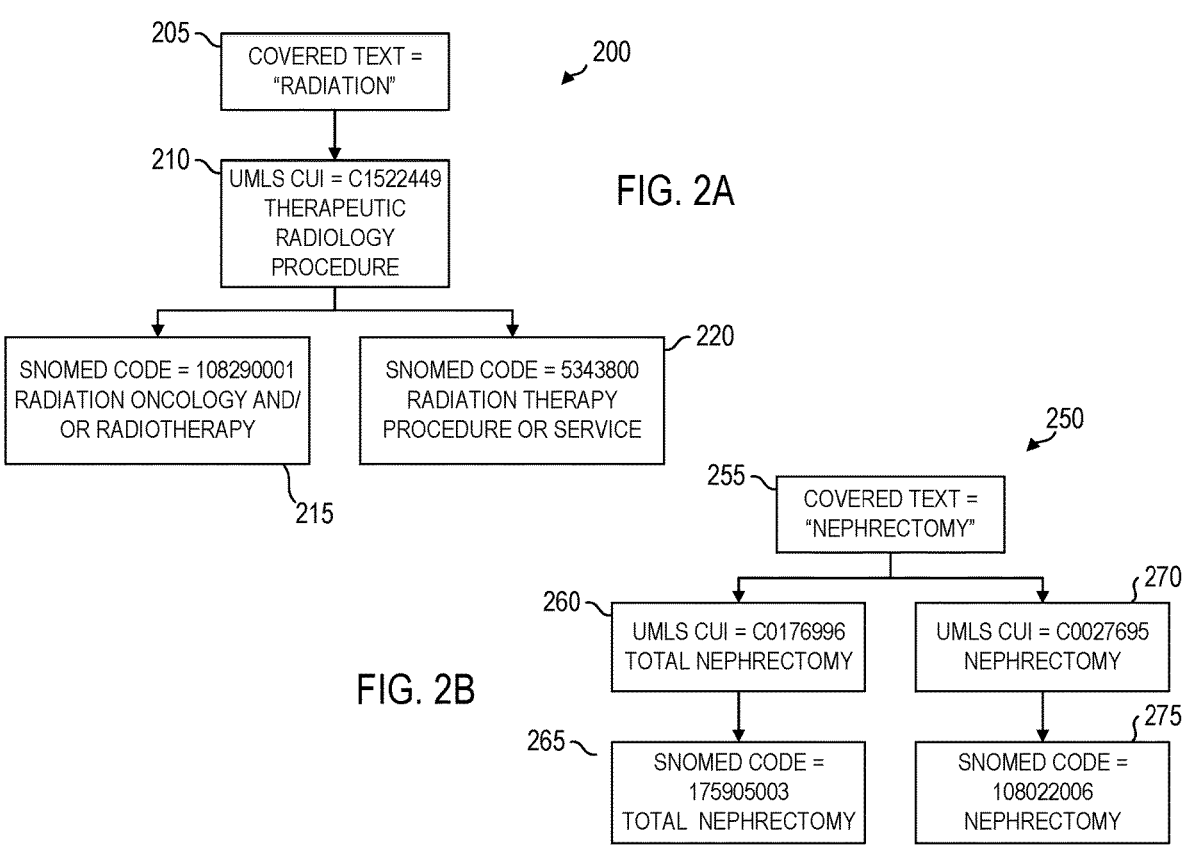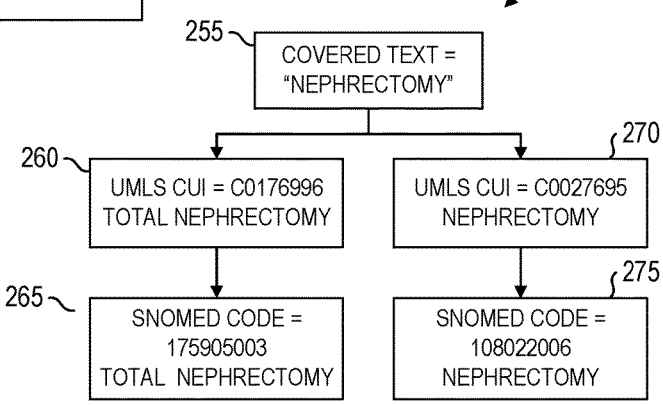

CODE POINT RESOLUTION USING NATURAL LANGUAGE PROCESSING AND METATHESAURUS

BACKGROUND

Disclosed herein is a system and related method for a code point resolution using natural language processing and a metathesaurus. In the medical domain, applications may use standardized medical terminology codes (SMTCs) to exchange clinical information. A common goal when processing unstructured patient notes is to produce SMTCs corresponding to the medical text. A common approach to extracting SMTCs from natural language is to use a biomedical metathesaurus that contains metathesaurus concept entities (MCEs), such as the Unified Medical Language System (UMLS) Metathesaurus (UMLSM). Concepts or meanings represented by MCEs that are found within the unstructured medical text may be detected using the vocabularies defined by the metathesaurus. The detected concepts may then be mapped to SMTCs using mappings in the metathesaurus and relevant MCEs.

SUMMARY

A method is provided for exchanging medical information with a medical management system. The method comprises receiving, using a processor of a code point resolver, from the medical management system, medical text via a network interface. A code point is a single standardized medical terminology code (SMTC) that corresponds to a medical concept contained within the medical text. The method further applies rule-based logic to process the medical text to form a localized mapping of a text portion of the medical text to a plurality of candidate SMTCs (CSMTCs) that are related to at least one metathesaurus concept entity (MCE) in a metathesaurus, and to determine the code point from the CSMTCs. The method transmits, via the network interface, to the medical management system, the code point.

A code point resolver is provided, comprising a memory, and a processor. The code point resolver is configured to receive, using a processor of a code point resolver, from the medical management system, medical text via a network interface. A code point is a single standardized medical terminology code (SMTC) that corresponds to a medical concept contained within the medical text. The code point resolver applies rule-based logic to process the medical text to form a localized mapping of a text portion of the medical text to a plurality of candidate SMTCs (CSMTCs) that are related to at least one metathesaurus concept entity (MCE) in a metathesaurus. The code point resolver determines the code point from the CSMTCs, and transmits, via the network interface, to the medical management system, the code point.

Furthermore, embodiments may take the form of a related computer program product, accessible from a computer-usable or computer-readable medium providing program code for use, by, or in connection, with a computer or any instruction execution system. For the purpose of this description, a computer-usable or computer-readable medium may be any apparatus that may contain a mechanism for storing, communicating, propagating or transporting the program for use, by, or in connection, with the instruction execution system, apparatus, or device.

BRIEF DESCRIPTION OF THE DRAWINGS

Various embodiments are described herein with reference to different subject-matter. In particular, some embodiments may be described with reference to methods, whereas other embodiments may be described with reference to apparatuses and systems. However, a person skilled in the art will gather from the above and the following description that, unless otherwise notified, in addition to any combination of features belonging to one type of subject-matter, also any combination between features relating to different subject-matter, in particular, between features of the methods, and features of the apparatuses and systems, are considered as to be disclosed within this document.

The aspects defined above, and further aspects disclosed herein, are apparent from the examples of one or more embodiments to be described hereinafter and are explained with reference to the examples of the one or more embodiments, but to which the invention is not limited. Various embodiments are described, by way of example only, and with reference to the following drawings:

FIG. 2A is a block diagram of a concept tree (alternately, "surface form") that illustrates an instance in which the text portion maps to a single CUI having multiple CSMTCs (e.g., SNOMED codes), according to some embodiments.

FIG. 2B is a block diagram that illustrates multiple CUIs due to ambiguity applying to the covered text, according to some embodiments.

DETAILED DESCRIPTION

The following general computer acronyms may be used below:

TABLE 1

General Computer Acronyms

| | |
|---|---|
| API | application program interface |
| ARM | advanced RISC machine |
| CD-ROM | compact disc ROM |
| CMS | content management system |
| CoD | capacity on demand |
| CPU | central processing unit |
| CUoD | capacity upgrade on demand |
| DPS | data processing system |
| DVD | digital versatile disk |
| EPROM | erasable programmable read-only memory |
| FPGA | field-programmable gate arrays |

TABLE 1-continued

General Computer Acronyms

| | |
|---|---|
| HA | high availability |
| IaaS | infrastructure as a service |
| I/O | input/output |
| IPL | initial program load |
| ISP | Internet service provider |
| ISA | instruction-set-architecture |
| LAN | local-area network |
| LPAR | logical partition |
| PaaS | platform as a service |
| PDA | personal digital assistant |
| PLA | programmable logic arrays |
| RAM | random access memory |
| RISC | reduced instruction set computer |
| ROM | read-only memory |
| SaaS | software as a service |
| SLA | service level agreement |
| SRAM | static random-access memory |
| WAN | wide-area network |

Data Processing System in General

Figure 1A:
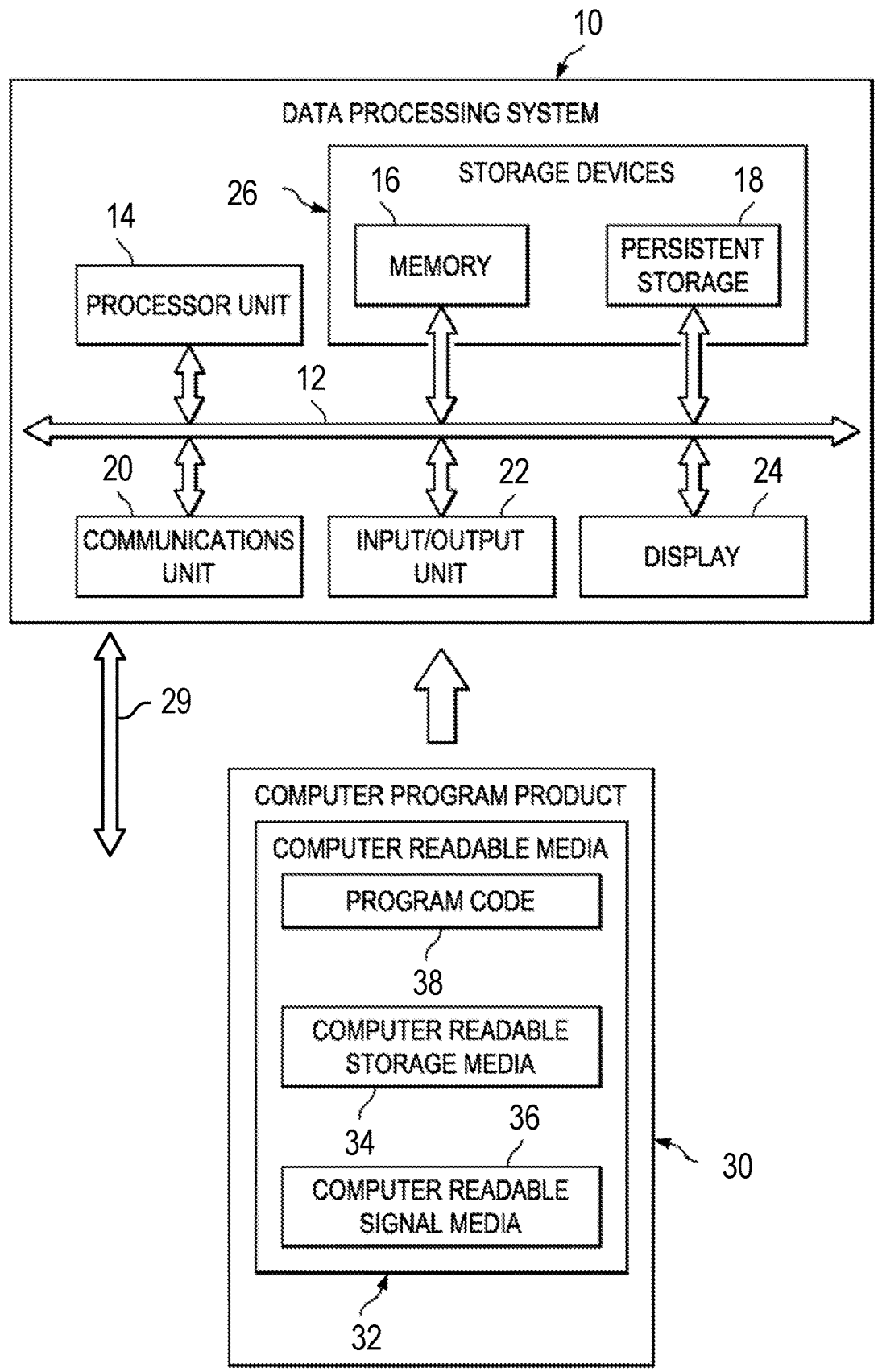
FIG. 1A is a block diagram of a data processing system (DPS) according to one or more embodiments disclosed herein.

FIG. 1A is a block diagram of an example DPS according to one or more embodiments. In this illustrative example, the DPS 10 may include communications bus 12, which may provide communications between a processor unit 14, a memory 16, persistent storage 18, a communications unit 20, an I/O unit 22, and a display 24.

The processor unit 14 serves to execute instructions for software that may be loaded into the memory 16. The processor unit 14 may be a number of processors, a multi-core processor, or some other type of processor, depending on the particular implementation. A number, as used herein with reference to an item, means one or more items. Further, the processor unit 14 may be implemented using a number of heterogeneous processor systems in which a main processor is present with secondary processors on a single chip. As another illustrative example, the processor unit 14 may be a symmetric multi-processor system containing multiple processors of the same type.

The memory 16 and persistent storage 18 are examples of storage devices 26. A storage device may be any piece of hardware that is capable of storing information, such as, for example without limitation, data, program code in functional form, and/or other suitable information either on a temporary basis and/or a permanent basis. The memory 16, in these examples, may be, for example, a random access memory or any other suitable volatile or non-volatile storage device. The persistent storage 18 may take various forms depending on the particular implementation.

For example, the persistent storage 18 may contain one or more components or devices. For example, the persistent storage 18 may be a hard drive, a flash memory, a rewritable optical disk, a rewritable magnetic tape, or some combination of the above. The media used by the persistent storage 18 also may be removable. For example, a removable hard drive may be used for the persistent storage 18.

The communications unit 20 in these examples may provide for communications with other DPSs or devices. In these examples, the communications unit 20 is a network interface card. The communications unit 20 may provide communications through the use of either or both physical and wireless communications links.

The input/output unit 22 may allow for input and output of data with other devices that may be connected to the DPS 10. For example, the input/output unit 22 may provide a connection for user input through a keyboard, a mouse, and/or some other suitable input device. Further, the input/ output unit 22 may send output to a printer. The display 24 may provide a mechanism to display information to a user.

Instructions for the operating system, applications and/or programs may be located in the storage devices 26, which are in communication with the processor unit 14 through the communications bus 12. In these illustrative examples, the instructions are in a functional form on the persistent storage 18. These instructions may be loaded into the memory 16 for execution by the processor unit 14. The processes of the different embodiments may be performed by the processor unit 14 using computer implemented instructions, which may be located in a memory, such as the memory 16. These instructions are referred to as program code 38 (described below) computer usable program code, or computer readable program code that may be read and executed by a processor in the processor unit 14. The program code in the different embodiments may be embodied on different physical or tangible computer readable media, such as the memory 16 or the persistent storage 18.

The DPS 10 may further comprise an interface for a network 29. The interface may include hardware, drivers, software, and the like to allow communications over wired and wireless networks 29 and may implement any number of communication protocols, including those, for example, at various levels of the Open Systems Interconnection (OSI) seven layer model.

FIG. 1A further illustrates a computer program product 30 that may contain the program code 38. The program code 38 may be located in a functional form on the computer readable media 32 that is selectively removable and may be loaded onto or transferred to the DPS 10 for execution by the processor unit 14. The program code 38 and computer readable media 32 may form a computer program product 30 in these examples. In one example, the computer readable media 32 may be computer readable storage media 34 or computer readable signal media 36. Computer readable storage media 34 may include, for example, an optical or magnetic disk that is inserted or placed into a drive or other device that is part of the persistent storage 18 for transfer onto a storage device, such as a hard drive, that is part of the persistent storage 18. The computer readable storage media 34 also may take the form of a persistent storage, such as a hard drive, a thumb drive, or a flash memory, that is connected to the DPS 10. In some instances, the computer readable storage media 34 may not be removable from the DPS 10.

Alternatively, the program code 38 may be transferred to the DPS 10 using the computer readable signal media 36. The computer readable signal media 36 may be, for example, a propagated data signal containing the program code 38. For example, the computer readable signal media 36 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, the program code 38 may be downloaded over a network to the persistent storage 18 from another device or DPS through the computer readable signal media 36 for use within the DPS 10. For instance, program code stored in a computer readable storage medium in a server DPS may be downloaded over a network from the server to the DPS 10. The DPS providing the program code 38 may be a server computer, a client computer, or some other device capable of storing and transmitting the program code 38.

The different components illustrated for the DPS 10 are not meant to provide architectural limitations to the manner in which different embodiments may be implemented. The different illustrative embodiments may be implemented in a DPS including components in addition to or in place of those illustrated for the DPS 10.

Cloud Computing in General

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1B:
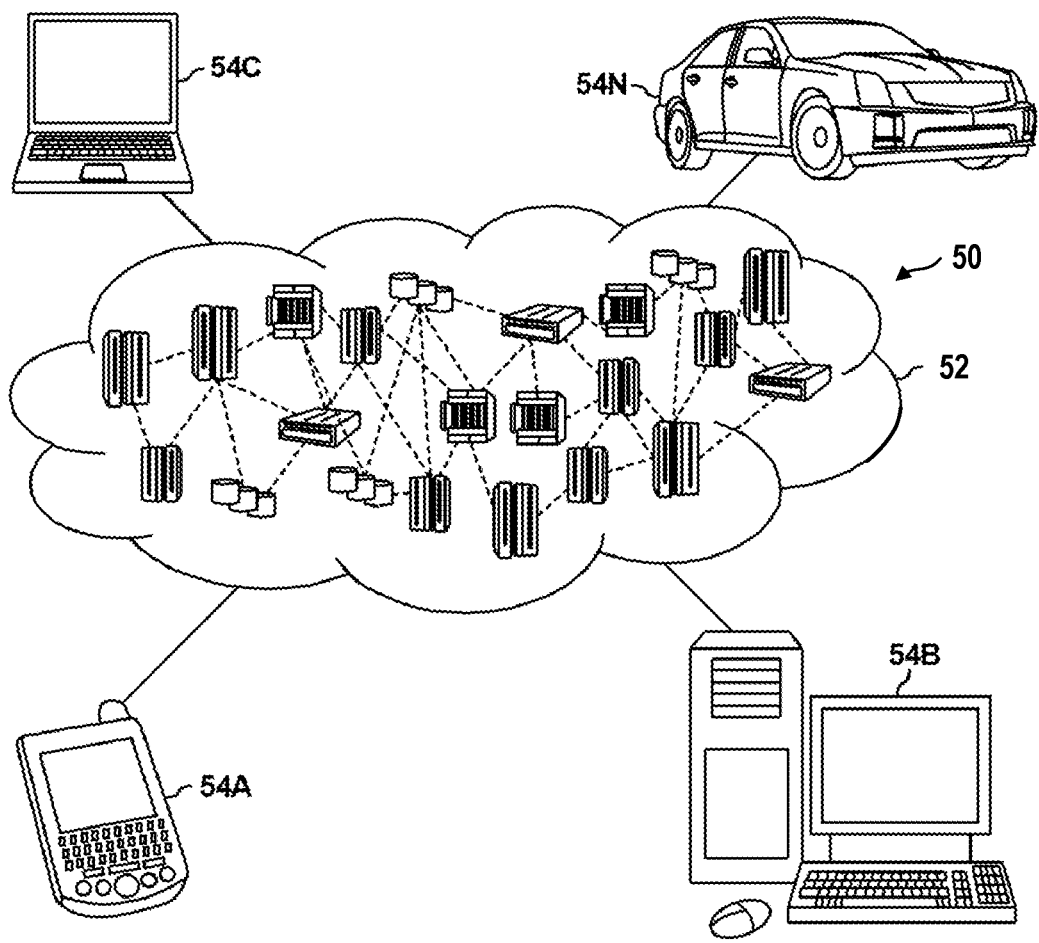
FIG. 1B is a pictorial diagram that depicts a cloud computing environment according to an embodiment disclosed herein.

Referring now to FIG. 1B, illustrative cloud computing environment 52 is depicted. As shown, cloud computing environment 52 includes one or more cloud computing nodes 50 with which local computing devices used by cloud consumers, such as, for example, personal digital assistant (PDA) or cellular telephone 54A, desktop computer 54B, laptop computer 54C, and/or automobile computer system 54N may communicate. Nodes 50 may communicate with one another. They may be grouped (not shown) physically or virtually, in one or more networks, such as Private, Community, Public, or Hybrid clouds as described hereinabove, or a combination thereof. This allows cloud computing environment 52 to offer infrastructure, platforms and/or software as services for which a cloud consumer does not need to maintain resources on a local computing device. It is understood that the types of computing devices 54A-N shown in FIG. 1B are intended to be illustrative only and that computing nodes 50 and cloud computing environment 52 can communicate with any type of computerized device over any type of network and/or network addressable connection (e.g., using a web browser).

Figure 1C:
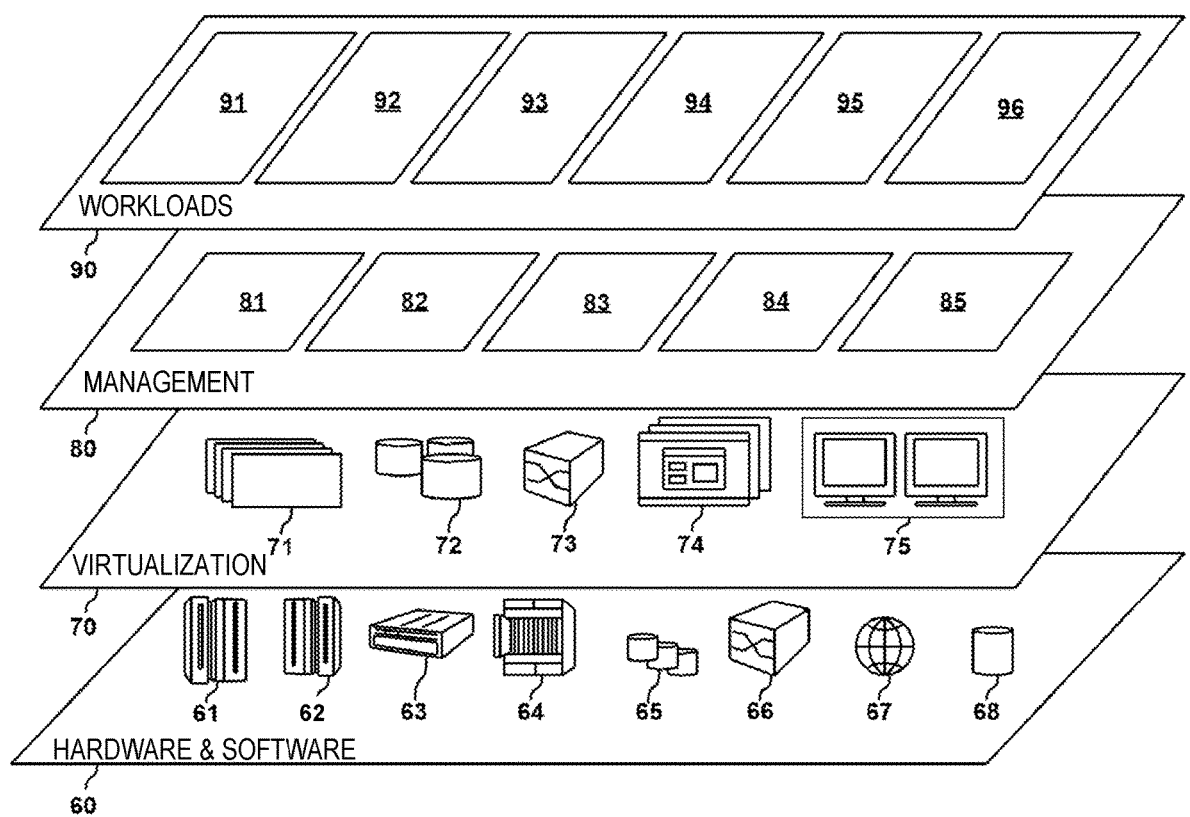
FIG. 1C is a pictorial diagram that depicts abstraction model layers according to an embodiment disclosed herein.

Referring now to FIG. 1C, a set of functional abstraction layers provided by cloud computing environment 52 (FIG. 1B) is shown. It should be understood in advance that the components, layers, and functions shown in FIG. 1C are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and application processing 96.

Any of the nodes 50 in the computing environment 52 as well as the computing devices 54A-N may be a DPS 10.

Computer Readable Media

The present invention may be a system, a method, and/or a computer readable media at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Technical Application

The one or more embodiments disclosed herein accordingly provide an improvement to computer technology. For example, an improvement to a computer database comprising medical information allows for a more efficient and effective resolution of ambiguity that may exist within the database.

Code Point Resolution Using Natural Language Processing and a Metathesaurus

The following application specific acronyms may be used below:

TABLE 2

Application Specific Acronyms

| ANSI | American National Standards Institute |
| CSMTC | candidate standardized medical terminology codes |
| CT | clinical terms |
| CUI | concept unique identifier |
| DICOM | Digital Imaging and Communications in Medicine |
| EMR | electronic medical record |
| HL7 | Health Level Seven International |
| IDC | International Classification of Diseases |
| ISO | International Organization for Standardization |
| LOINC | Laboratory Logical Observation Identifiers Names and Codes |

TABLE 2-continued

Application Specific Acronyms

| MCE | metathesaurus concept entity |
| NCCN | National Comprehensive Cancer Network |
| NLP | natural language processing |
| OPCS-4 | Office of Population Censuses and Surveys Classification of Interventions and Procedures version 4 |
| PET | positron emission tomography |
| SMTC | standardized medical terminology codes, for example, SNOMED |
| SNOMED | Systematized Nomenclature of Medicine |
| UMLS | Unified Medical Language System |
| UMLSM | Unified Medical Language System metathesaurus |

The use of MCEs and SMTCs are known in the medical industry. However, there may be instances in which multiple concepts and related MCEs are present in a span of medical text, or instances in which a single concept may map to multiple SMTCs (a one-to-many relationship). Having multiple concepts and related MCEs or multiple SMTCs may result in a lack of clarity or produce ambiguity, and thus, it may be desirable to eliminate the multiplicity and provide a single MCE and/or SMTC. The process of ultimately producing a single SMTP from a span of medical text is referred to herein as "code point resolution". Code point resolution means selecting a single SMTC from among multiple candidate SMTCs (CSMTCs) for a given portion of medical text that is most appropriate to a particular application that will use the information, or domain for the solution. By way of example, if a term "radiation" were found in clinical notes with a clinical application, the system would consider codes related to "radiation therapy" (treatment) before considering "ionizing radiation" (physical force), which would not be associated with clinical notes very often.

Disclosed herein is a code point resolver system and related method that may be used to resolve a code point for one or more concepts over a span of unstructured medical text. Code point resolution by the code point resolver may be performed by considering concepts or associated MCEs that are a best fit for an application, and mapping an individual MCE(s) to a single code point. In the case where multiple MCEs cause multiple SMTCs to be CSMTCs, the code point resolver may use other information, such as clinical notes and/or structured data to disambiguate. "Medical text", "clinical notes", and "other information" may, in some cases, have a similar form, but may constitute separate documents or be delineated in some manner, such as having different origins or being part of a separate entry and the like. "Clinical notes", as defined herein, refers to a wide variety of documents generated on behalf of a patient, and may include, but is not limited by, the FHIR definition of clinical notes. Usually, each note is for a specific event, such as a consultation, discharge, procedure, etc. When multiple CSMTCs still exist, the process may, in some embodiments, determine a fitness score for each CSMTC and then determine the code point as the one CSMTC having the highest fitness score. Other techniques discussed herein may be utilized to determine the code point as well. If structured data is available for the patient, information in that structured data may be utilized in addition to the (unstructured) medical text for improving accuracy. "Medical text" may additionally include research papers, clinical trial protocols, or other data not related to a specific patient.

Code point resolution relates to concept detection and mapping these concepts to concept codes, i.e., the SMTCs, such as the Systematized Nomenclature of Medicine—Clinical Terms (SNOMED-CT) codes, using the approaches and techniques described herein, to reach a decision as to which CSMTC best represents the information in a span or portion of medical text. Other SMTCs may involve terminologies such as the International Classification of Diseases (ICD) ICD-9-CM, ICD-10, ICD-O-3, ICD-10-AM, Laboratory Logical Observation Identifiers Names and Codes (LOINC), RxNorm, which is part of the UMLS terminology, and the Office of Population Censuses and Surveys Classification of Interventions and Procedures version 4 (OPCS-4). The SMTCs may support standards such as the American National Standards Institute (ANSI), the Digital Imaging and Communications in Medicine (DICOM), Health Level Seven International (HL7), and the International Organization for Standardization (ISO) standards. The SNOMED-CT, as a particular instance of a SMTC system, is a standardized vocabulary of clinical terminology that is widely used by health care provides for the electronic exchange of clinical health information. SNOMED codes are a common standard for exchanging clinical information between providers. SNOMED-CT codes tend to focus on clinical information. Because of that, SNOMED-CT is often used by care providers and insurance companies for exchanging structured medical information, and thus it is more standard in the industry for "end users".

The techniques described herein may involve natural language processing (NLP), and may be practiced, for example, without user interaction. They may disambiguate SMTCs for MCEs detected from the medical text "in context", i.e., using relationships provided in the metathesaurus and context information from external sources, such as available clinical notes (which, e.g., may be broader than just nearby words in a given medical text item).

The UMLS includes a biomedical metathesaurus, the UMLSM, that is organized by concept/meaning, and links similar names (or surface forms) for a particular concept from nearly two-hundred vocabularies. A "concept" is a fundamental unit of meaning in this metathesaurus, which represents a single meaning—every concept is assigned a concept unique identifier (CUI). This metathesaurus also identifies useful relationships between concepts and preserves the meanings and relationships from each vocabulary. Solutions often summarize clinical information as SMTCs, such as SNOMED codes, making use of detected CUIs and relationships defined by the metathesaurus.

The UMLS CUIs are generally used by NLP related tasks to extract meaning from text. UMLS is built from over one-hundred different vocabularies (including SNOMED). Mappings between vocabs get complicated quickly. A single surface form may have multiple possible meanings (CUIs), each CUI may be associated with zero or more SNOMED codes, and SNOMED codes may be associated with more than one CUI/concept. This results is an n-to-n relationship between UMLS CUIs and SNOMED codes that makes it difficult to get from a word or phrase to the ideal SNOMED code or codes that can be used by a higher level application. By way of example, "muscle weakness" vs. "incomplete paralysis" are concepts in different vocabs that might be a single concept in one vocab, and multiple concepts in another. The UMLS tends to provide the mappings and the consumer figures out what to do with them, and thus, it is not a practical tool for end users or high level systems. An aim herein is then to find a single SMTC, such as a SNOMED code, that is most useful to the consumer/application for the medical text.

FIG. 2A is a block diagram of a concept tree 200 (alternately, surface form) that illustrates an instance in which the text portion maps to a single CUI having multiple CSMTCs (e.g., SNOMED codes). The concept tree 200 shows a relationship between a key word(s) of a medical text portion, one or more related CUIs, and one or more SMTCs. The concept tree 200 may have a "covered text" field 205 that indicates the relevant text for a medical text portion. In the example shown, a medical text (described below) input portion may be "the patent received radiation treatment", resulting in the covered text being "radiation". The relevant single UMLS CUI 210 meaning is designated "C1522449" from the metathesaurus in this example, which corresponds to the concept/meaning of a therapeutic radiology procedure. However, this CUI may be related to two SMTCs: a first SMTC 215, such as a first SNOMED code (here, by way of example, 108290001 corresponding to radiation oncology and/or radiotherapy), and a second SMTC, such as a second SNOMED code (here, by way of example, 5343800 corresponding to radiation therapy procedure or service).

There are reasons that multiple SMTCs may be relevant. Although the single CUI in 000this example represents a single meaning, each CUI may map to zero or more SMTCs. It may map to zero SMTCs because it is possible that no SMTC is defined for the particular meaning; it is also possible that multiple SMTCs could apply to the meaning. For example, if the CUI for "Therapeutic Radiology Procedure" is discovered for the text "radiation", there are two SNOMED codes that are mapped to the CUI.

Multiple CUI—Ambiguity

FIG. 2B is a block diagram that illustrates multiple CUIs due to ambiguity applying to the covered text. A single medical text span or medical text portion may have multiple relevant UMLS concepts defined for it. The UMLS is a combination of many vocabularies, and these vocabularies may not agree on a specific meaning. This is partly because a single surface form might have different meanings in different contexts. For example, in FIG. 2B, "nephrectomy" could refer to a total nephrectomy in one context, or any type of nephrectomy in another context. In this example, each CUI has a distinct SNOMED code mapped to it. As shown, the concept tree 250 has a "covered text" field 255 that indicates the covered text is "nephrectomy". The first UMLS CUI 260 meaning is designated "C0176996" which means a total nephrectomy. This is related to a first SMTC 265, such as a first SNOMED code (here, by way of example, 175905003). The second UMLS CUI 270 meaning is designated "C0027695" which means a nephrectomy. This is related to a second SMTC 275, such as a second SNOMED code (here, by way of example, 108022006).

Multiple CUI—Combination of Ideas/Multiple Concepts

Figure 3A:
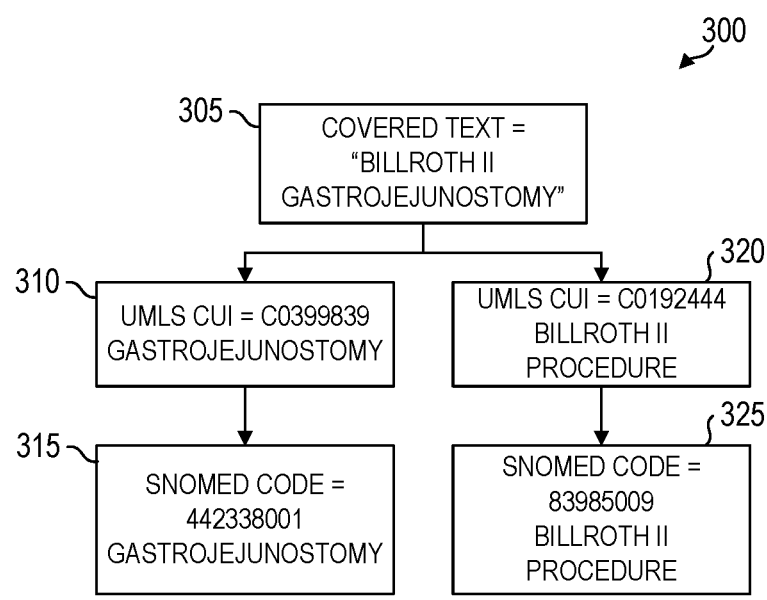
FIG. 3A is a block diagram of a concept tree that combines multiple ideas, which is another reason that multiple concepts may exist, according to some embodiments.

FIG. 3A is a block diagram of a concept tree 300 that combines multiple ideas, which is another reason that multiple concepts may exist. In this example, the concept tree 300 represents a combination of ideas, and the combination does not have a single UMLS CUI. FIG. 3A illustrates an example concept tree 300 in which the covered text field 305 includes a combination of ideas: "BillRoth II" and "GastroJejunostomy". Here, the first UMLS CUI 310 meaning is designated "C0399839" which means a gastrojejunostomy. This is related to a first SMTC 315, such as a first SNOMED code (here, by way of example, 442338001). The second UMLS CUI 320 meaning is designated "C0192444" which means a BillRoth II procedure. This is related to a second SMTC 325, such as a second SNOMED code (here, by way of example, 83985009).

Increased Complexity

Figure 3B:
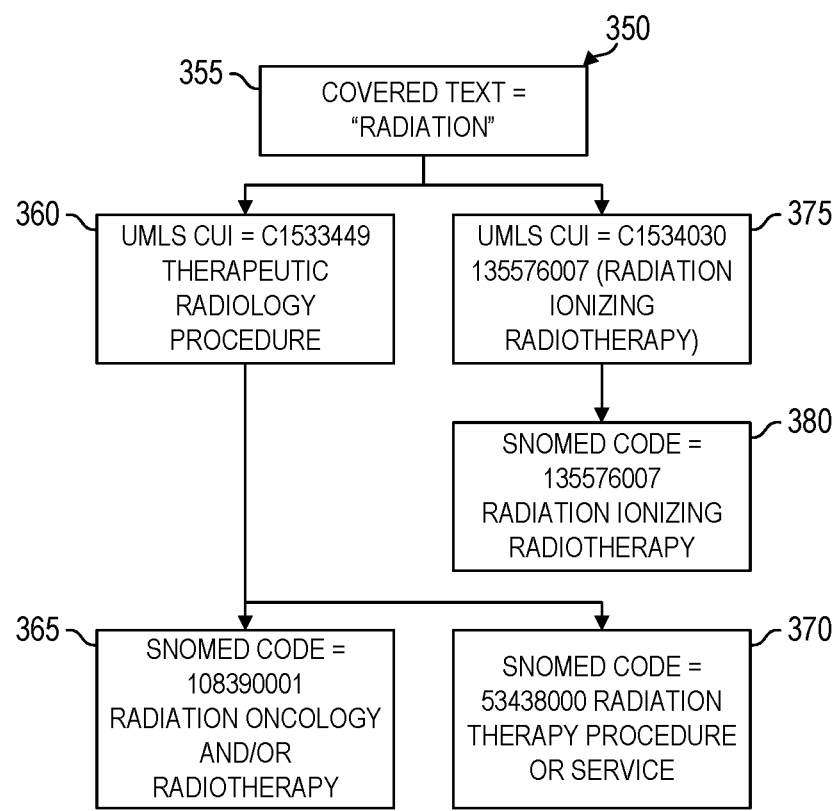
FIG. 3B is a block diagram that illustrates a concept tree for an example of increased complexity, according to some embodiments.

In practice, these examples may combine to create enormous complexity. FIG. 3B is a block diagram that illustrates a concept tree 350 for an example of increased complexity.

For example, in FIG. 3B, the covered text field 355 includes the term "radiation", which has multiple CUIs: one with multiple SNOMED codes, and one with a single SNOMED code. Here, the first UMLS CUI 360 meaning is designated "C1533449" which means a therapeutic radiology procedure. This is related to two SMTCs: a first SMTC 365, such as a first SNOMED code (here, by way of example, 108390001 for radiation oncology and/or radiotherapy), and a second SMTC 370, such as a second SNOMED code (here, by way of example, 53438000 for a radiation therapy procedure or service). The second UMLS CUI 375 meaning is designated "C1534030" which means radiation ionizing radiotherapy. This is related to a third (single) SMTC 380, such as a second SNOMED code (here, by way of example, 135576007). Far more complex concept trees are possible by invoking this principle. The result is a significant increase of SMTCs associated with a single event.

Figure 4A:
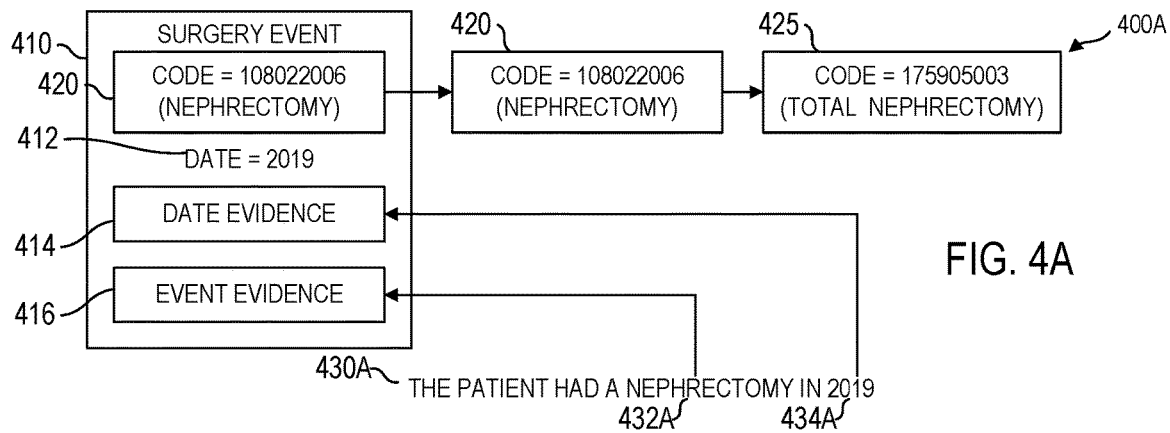
FIGS. 4A-4C are block diagrams illustrating process flows for associating a best-fit SMTC with a respective event, according to some embodiments.
Figure 4B:
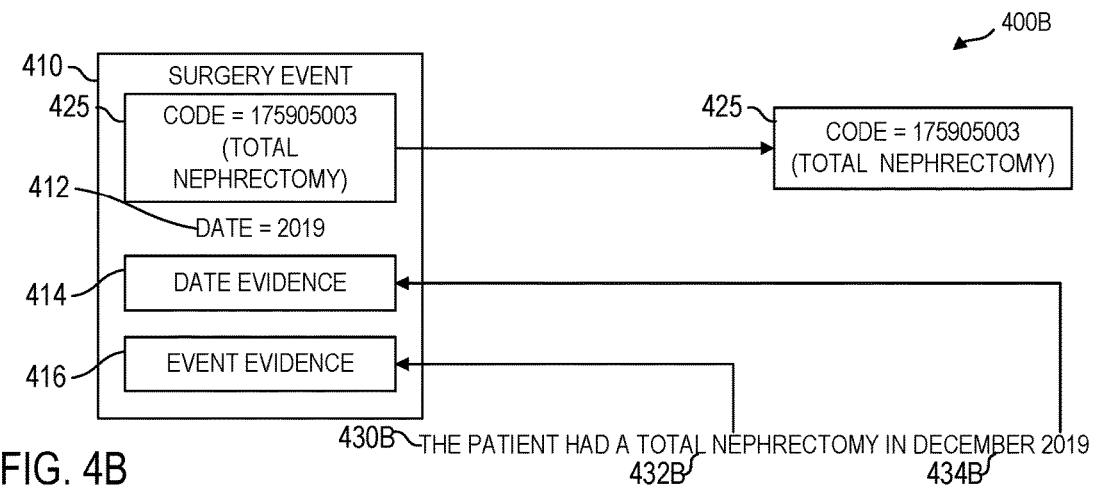
Figure 4C:
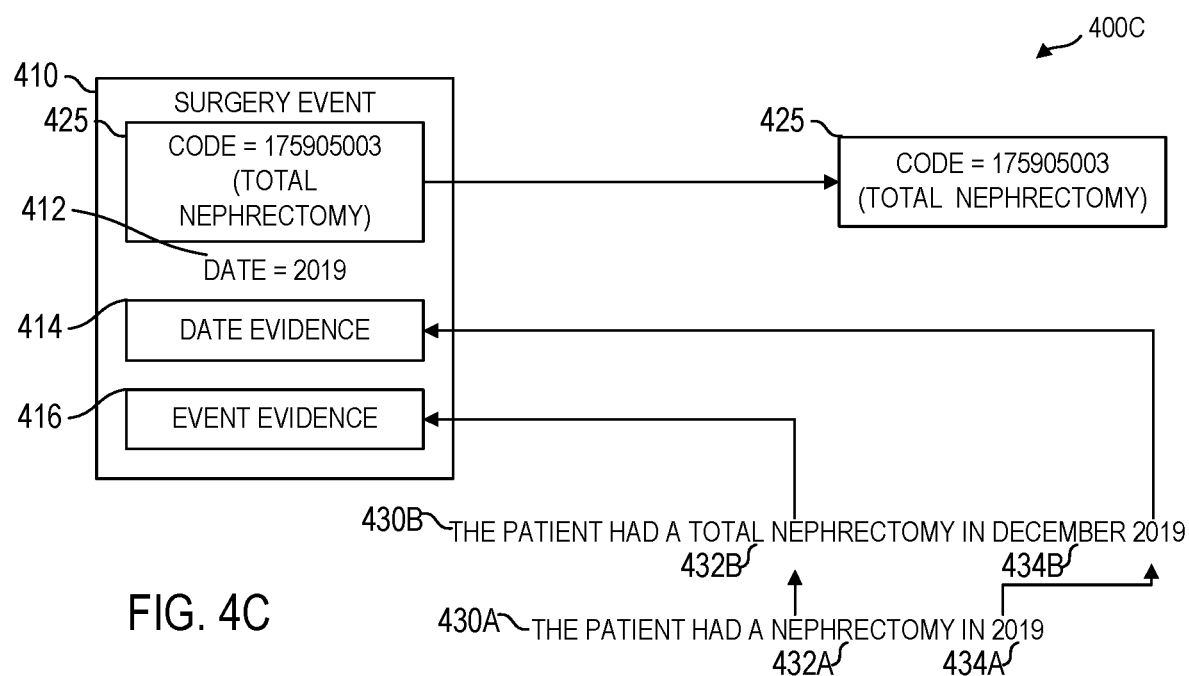

FIGS. 4A-4C are block diagrams illustrating process flows 400A, 400B, 400C for associating a best-fit SMTC with a respective event.

Figure 5:
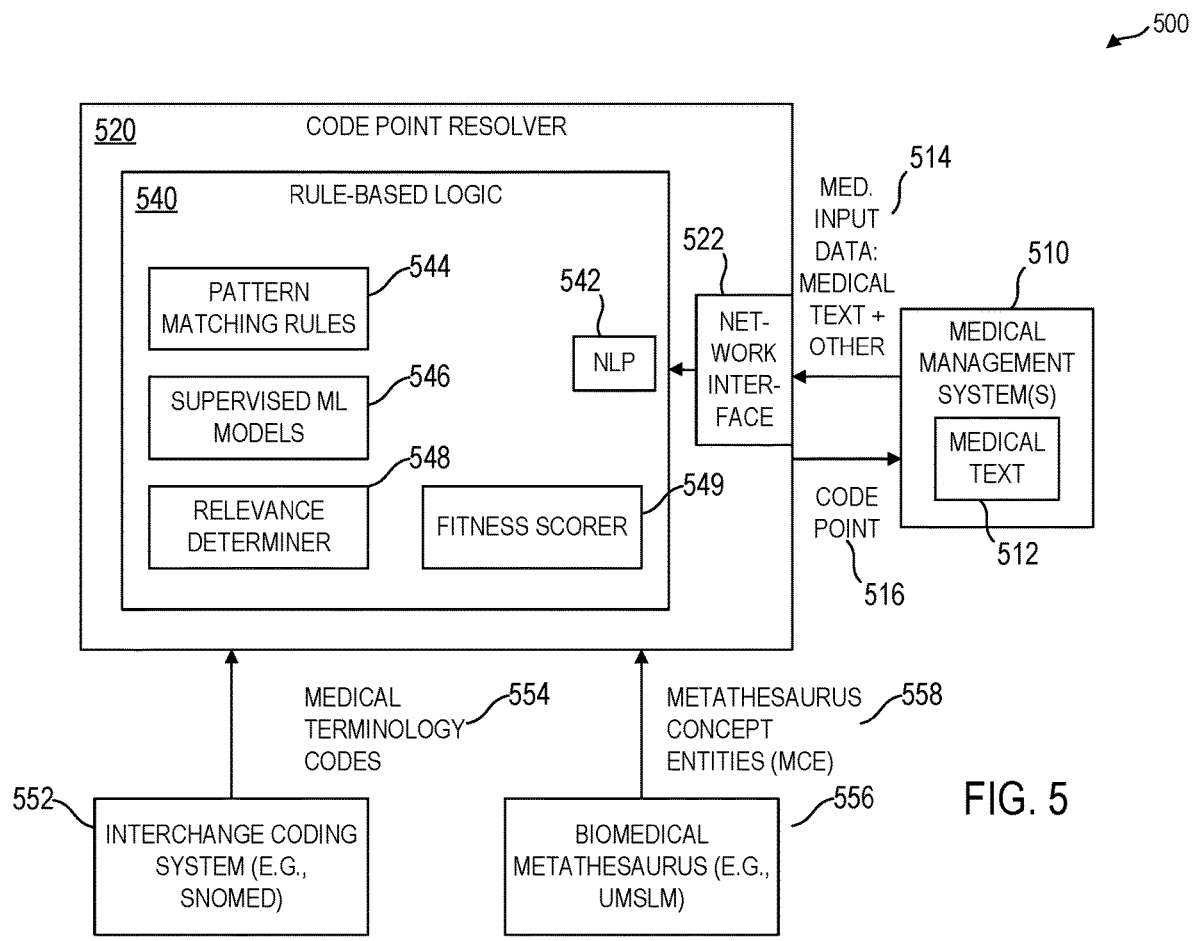
FIG. 5 is a block diagram illustrating a system within which the code point resolver may operate, according to some embodiments.

FIG. 5 is a block diagram illustrating a system 500 within which the code point resolver 520 may operate. As shown in FIG. 5, medical input data 514, including the medical text 512, may originate from a medical management system 510. The medical management system 510 may comprise any number of computers, such as DPSs 10, that are connected via a network, and may be implemented, for example, in a cloud computing environment 52. The code point resolver 520 may operate with the application processing 96, as described above. The medical input data 514 may comprise medical text 512 and related other information, such as clinical notes and structured data, may be all or a part of an electronic medical record (EMR). The medical input data 514 may be received by the code point resolver 520 via a network interface 522, and received by rule-based logic 540, which may comprise an NLP 542, pattern matching rules 544, supervised machine learning (ML) models 546, or any other rule-based mechanism. Where supervised ML models 546 are used, such models may be trained in a training phase using a set of training data that relates medical text to SMTCs and/or provides selecting a single SMTC from a set of SMTCs. The rule-based logic 540 may comprise a knowledge base that stores relationships and mappings between CUIs and SMTCs.

In some embodiments, the medical text 512 may be broken down into medical text portions. For example, if the medical text 512 contains information from multiple visits to a facility, multiple procedures performed, etc., the NLP 542 may break the information into individual portions to simplify the processing. This breaking down or parsing of the medical text 512 by the NLP 542 may be based on a mechanism such as punctuation, keywords, parts of language (nouns, verbs, etc.) or using other known techniques for language parsing. The medical text portions may be further processed by the NLP 542 to remove superfluous words and organize the text in a consistent manner. Additionally, the NLP 542 may perform a tokenization of the medical text 512. The NLP 542 may determine one or more concepts/CUIs associated with the medical text 512 or text portions.

The code point resolver 520, in order to resolve the code point, i.e., the best-fit SMTC, may consider multiple concepts/CUIs that are the best fit for an application. The code point resolver 520 may determine that certain concepts and/or certain types of concepts are more valuable for a medical text portion 512 than others. The rule-based logic 540 may make this determination by incorporating NLP 542, pattern matching rules 544, and/or supervised machine learning models 546. By way of example, if the algorithm 540 has a relevance determiner 548 that determines a medical text portion 512 relates to a radiation procedure, then it would determine applicable CUIs that are therapeutic or preventive procedures. Since this relates to a procedure, non-procedure-based concepts (such as the concept for "electromagnetic radiation" or "radiation physical force") may thus be considered not relevant and filtered out and not considered for mapping into an SMTC(s), since it is much more likely that documentation of a clinical visit is referring to a type of radiation therapy. The delineation of a procedure vs. non-procedure may be, for example, found in definitions of the SMTCs themselves, or may be distinguished by being "therapeutic and diagnostic procedures" as opposed to something that is for example a "physical object" (e.g., a positron emission tomography (PET) scan vs PET system).

In addition to the distinction of "procedure vs. non-procedure", other forms of distinction may be considered as well. For example, "disorder vs. organism" might be a distinction that could be used to delineate various terms, such as SARS, where the text could potentially refer to either a disorder or an organism. In some embodiments, the surface form matching logic uses the longest match it can find.

In some embodiments, the individual concepts are mapped to a code point. The code point resolver 520 determines the code point for a CUI by applying the rule-based logic 540 that considers common parameters of an application. The rule-based logic 540 may thus use the relevance determiner 548 to select an SMTC or filter SMTCs based on the most correct intent of the CUI in the context of the medical application (e.g., codes for procedures are favored over codes for non-procedures or other intents) that may be provided to the code point resolver 520. Although the relevance determiner 548 is show separately from the pattern matching rules 544 and the supervised machine learning models 546, the relevance determiner 548 may make use of them or be a part of them. Similarly, the fitness scorer 549, discussed in more detail below, may make use of the pattern matching rules and/or supervised ML models 546 or be a part of them. The code point resolver 520 may have access to external data information sources, such as the interchange coding system 552 (e.g., SNOMED and others discussed above) to provide the SMTCs 554, and a biomedical metathesaurus 556 (e.g., UMLSM discussed above) to provide the metathesaurus concept entities 558.

If multiple CSMTCs remain, and these codes exist in a hypernym-hyponym relationship, then the rule-based logic 540 may choose the hypernym over the hyponym. The case in FIG. 2B illustrates this. "Nephrectomy" could be mapped to "total nephrectomy" or "nephrectomy". Since there is uncertainty at this point, the more general one is picked. But if other documents later include medical text about a "total nephrectomy" on the same day, then that decision may be revised to a more specific code. In another example, "mastectomy" may be chosen as the hypernym, but could be later determined to refer to other kinds of mastectomies (e.g., simple, radical, bilateral . . . ). These examples are largely based on how UMLS and SNOMED organize the relationships between procedures. The mastectomy could be viewed as an example of speaking generally about something more specific. However, in terms of code resolution, this problem may also happen because different vocabs have different mappings. Sometimes this leads to more than one mapping for the same medical text, and therefore it may be desirable to pick the most general concept for accuracy.

If multiple CSMTCs continue to remain, then a source rater may determine a reliability of the sources for the respective CSMTCs, and the CSMTC with the highest reliability rating. Because UMLS has many vocabularies and mappings, some sources are more reliable. If multiple CSMTCs continue to remain, then further logic may apply, such as the oldest CUI that exists in UMLS being chosen. Older CUIs are more familiar, and are more often used in practice. To determine the age of a CUI, it may be possible to determine an absolute or possibly a relative age based on a length or a value of the CUI (e.g., newer CUIs may have longer identifiers). In other embodiments, the age might be determined by loading each version of the UML's database and recording when a particular CUI first appeared in the database. In some embodiments, age is used as a proxy for how frequently a code is used, based on a presumption that CUIs that have been around a while are more in use than newer ones. Determining the frequency that a CUI or SMTC is used within a large corpus may be an alternative mechanism for decision-making.

As noted above, in the case where multiple concepts have resulted in multiple CSMTCs, the code point resolver 520 may try to disambiguate using other information, such as clinical notes or structured data. The code point resolver 520 will often detect a same event for a particular SMTC in multiple notes associated with the text portion. Some of these notes have more detail than others. For example, an operative clinical note may state a specific "skin-saving mastectomy", while an assessment clinical note may simplify this and simply state in a general manner that the patient had a "mastectomy". These operative and assessment clinical notes may be aggregated together by the code point resolver 520, and SMTC disambiguation may be performed at that time. In order for the code point resolver 520 to aggregate events or information from different text portions, it may consider identifying information related to the events, relationships between SMTCs and CSMTCs, as well as any detected date for the event. Further, the code point resolver 520 may then decide whether to combine the information from two events or not. If events are combined, then the most suitable code, based on the process discussed above, may be selected for the combined event.

By way of example, for the mastectomy example above, the code point resolver 520 may determine that the patient identifier is the same for two events represented by text portions, and the two clinical notes are both for the same day (or within a predefined segment of time), and thus logically determine that these two different notes both refer to the same event. Other rules or logic may be used to make this determination by the rule-based logic 540.

FIGS. 4A-4C are block diagrams illustrating process flows for associating a best-fit SMTC with a respective event, according to some embodiments.

FIG. 4A is a block diagram illustrating an event 400A for processing an event with ambiguous CSMTCs 420, 425. The medical input data 514 relates to a surgery event 410 having a first possible CSMTC 420, where the CSMTC refers to a nephrectomy, and a second possible CSMTC 425 refers to a total nephrectomy. The date evidence 414 associated with the surgery event 410 indicates the date of occurrence simply as being some time in 2019. The event evidence 416 makes reference to a generic "nephrectomy". As can be seen by the medical text 430A, the indication is that "the patient had a nephrectomy" 432A "in 2019" 434A.

FIG. 4B is a block diagram illustrating an event 400B that shows another event that has been constructed from a different text portion showing more detail, namely, the text portion clarifies that "the patient had a total nephrectomy" 432B and has a more specific "December 2019" 434B date. It also has a single CSMTC 425. The event in FIG. 4B can be combined with the event in FIG. 4A based on a relatedness of the procedures and relatedness of the date, even though one is more general than the other.

FIG. 4C is a block diagram illustrating a combination 400C of the events 400A, 400B from FIG. 4A and FIG. 4B. The most specific code 425, the total nephrectomy, has been selected for the new event by the rule-based logic 540, based on the more specific text portion 430B, 432B. The most specific date 434B has also been updated by the rule-based logic 540. The evidence from the two prior events 400A, 400B may be included in the new event 400C.

Returning to FIG. 5, a fitness score may be determined by the rule-based logic 540 in the event that the code point 516 cannot be determined by other mechanisms described herein. The rule-based logic 540 may utilize a fitness scorer 549 for each of the CSMTCs and then choose the CSMTC having the highest score. The fitness scorer may perform certain of the rule-based logic 540 described above, such as providing a higher score to a hypernym over a hyponym, providing a higher score for a UMLS or SMTC that is more reliable or has a higher reliability measure, providing a higher score where an older UMLS is present. A reliability measure for various sources may be provided in the configuration files of the code point resolver 520, and may be determined from developer experience, and combined potentially with measuring the accuracy of the overall system. When choosing mappings between UMLSs and SMTCs, some sources of the mapping are known or believed to be better sources than others.

In the event that no other principled logic yields a single CSMTC, then an arbitrary decision may be made by the rule-based logic 540 to ensure a single CSMTC is returned as the code point 516. This arbitrary decision may be based on, e.g., a numerical order of a SNOMED ID value, a random selection of remaining CSMTCs, or any other mechanism to ensure a return of a single value. In some embodiments, it may be advantageous to ensure a consistent return of the code point 516 for a given input of data.

Multiple factors discussed above may be used by the fitness scorer 549 to determine the fitness score, and these may be applied, in some embodiments, by applying a weighting to the factors described above. For example, a weighting may be applied to an MCE that is based on a medical application intent (e.g., a procedure may have a higher weighting than a test); a weighting might be applied in which hypernyms are weighted higher than hyponyms; a source that is more reliable may be weighted higher than one that is less reliable; and a weighting may be weighted according to codes by an industry acceptance rating.

Figure 6:
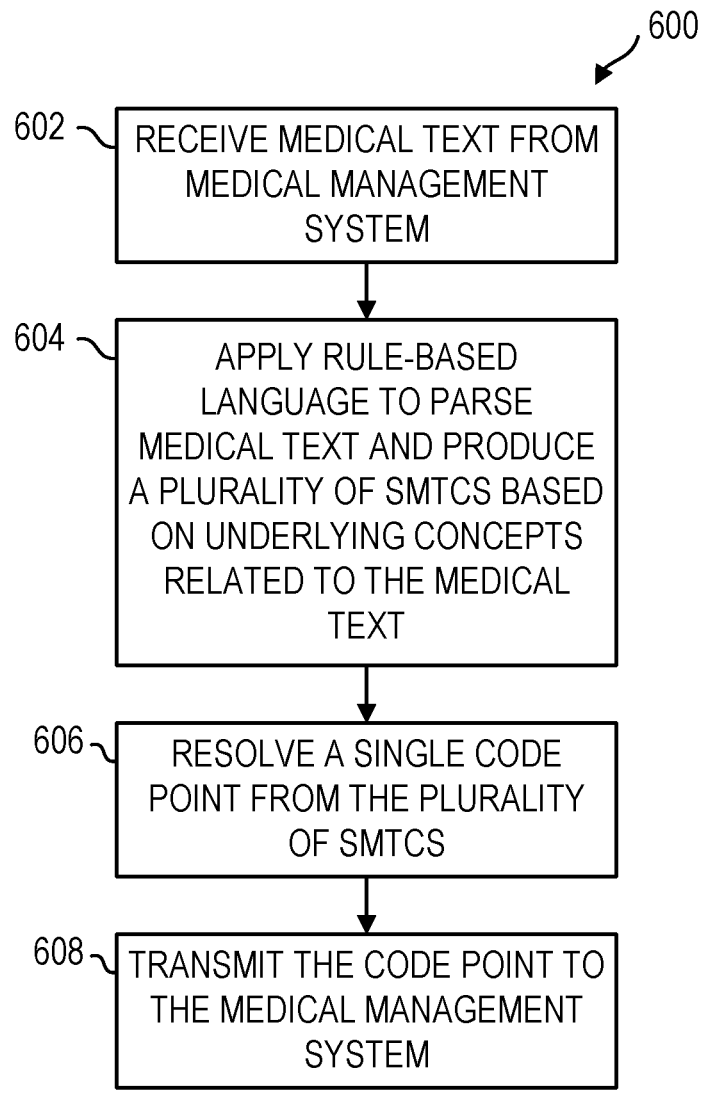
FIG. 6 is a flowchart illustrating a process that may be used with the code point resolver, according to some embodiments.

FIG. 6 is a flowchart of an example process 600 that may be utilized by the code point resolver 520. In operation 602, the code point resolver 520 receives, via a network interface 522, medical input data 514 that may comprise medical text 512, with possibly other information, from a medical management system 510. In operation 604, rule-based logic 540 may be used to process the medical text 512, and may comprise, in some embodiments, the components of a natural language processor 542, pattern matching rules 544, supervised ML models 546, a relevance determiner 548, and a fitness scorer 549. These components may interact with one another or share algorithms and functionality.

The rule-based logic 540 may utilize other information, such as clinical reports, and structured data, along with medical terminology codes (SMTCs) 554 or an interchange coding system 552, such as SNOMED. The rule-based logic may further utilize a biomedical metathesaurus, such as the UMLSM 556 to provide metathesaurus concept entities 558. A plurality of CSMTCs are associated with the medical input data 514. Ultimately, in operation 606, the code point resolver 520 resolves a single code point 516 from the plurality of CSMTCs. In operation 608, the code point 516 is transmitted, via the network interface 522, to the medical management system 510 in order to assist the medical management system 510 in resolving any ambiguity that may be present in the initial medical input data 514. The code point 516 may be further utilized to construct a timeline of a patient's history. By way of example, this could be used by an oncology application that assists a physician with following National Comprehensive Cancer Network (NCCN) guidelines, and/or matching patients with relevant clinical trials. Additionally, the code point 516 may be utilized to convert the unstructured text and other associated medical input data 514 into structured data, such as into a Fast Healthcare Interoperability Resources (FHIR) record format for storage and use in the above-discussed applications.

What is claimed is:

1. A method of exchanging medical information with a medical management system, comprising:
   receiving, using a processor of a code point resolver, from the medical management system, medical text via a network interface, wherein a code point is a single standardized medical terminology code (SMTC) that corresponds to a medical concept contained within the medical text;
   applying rule-based logic to process the medical text to form a localized mapping of a text portion of the medical text to a plurality of candidate SMTCs (CSMTCs) that are related to at least one metathesaurus concept entity (MCE) in a metathesaurus and to determine the code point from the CSMTCs, wherein applying rule-based logic comprises:
      determining a fitness score with a fitness scorer of the rule-based logic for each of the CSMTCs using weightings that are based on a medical application intent, a hypernym and hyponym relationship, a source reliability measure, and codes determined by an industry acceptance rating; and
      determining the code point by selecting a best-fit SMTC having a highest fitness score of the CSMTCs; and
   transmitting, via the network interface, to the medical management system, the code point.

2. The method of claim 1, wherein the medical text represents a medical application.

3. The method of claim 1, further comprising:
   parsing, with a natural language processor (NLP) of the rule-based logic, the medical text into one or more concepts that are each associated with one or more of the CSMTCs.

4. The method of claim 3, further comprising:
   using the NLP to parse the medical text into medical text portions based on a mechanism selected from the group consisting of punctuation, keywords, and parts of language.

5. The method of claim 1, wherein determining the fitness score comprises utilizing an additional element that is separate from the medical text and is selected from the group consisting of clinical notes and structured data.

6. The method of claim 1, wherein the SMTCs are based on one or more MCEs.

7. The method of claim 1, further comprising filtering, using a relevance determiner of the rule-based logic, the CSMTCs based on a type of medical application.

8. The method of claim 1, wherein the weighting for the medical application intent is greater for a procedure than for a non-procedure.

9. The method of claim 1, wherein the weighting for the hypernym and hyponym relationship is greater for the hypernym than for the hyponym.

10. The method of claim 1, wherein the weightings are proportional to a source reliability measure.

11. The method of claim 1, wherein the SMTC is based on an interchange coding system selected from the group consisting of SNOMED, LOINC, and RxNorm.

12. The method of claim 1, further comprising:
    receiving medical input data in addition to the medical text that comprises a first clinical note, a second clinical note different from the first clinical note, and at least one structured data element; and
    merging, using the rule-based logic, medical input records from two elements selected from the group consisting of the first clinical note, the second clinical note, and the structured data element, based on dates of the medical input records having compatible codes.

13. The method of claim 1, wherein the weightings are applied as a sequence of rules of the rule-based logic to the CSMTCs, wherein the sequence comprises:
    applying a relevance determiner to the CSMTCs to generate a first filtered set of CSMTCs;
    determining if the first filtered set of CSMTCs comprises more than one CSMTC;
    in response to the first filtered set of CSMTCs comprising more than one CSMTC, applying a weighting to the first filtered set of CSMTCs based on the hypernym and hyponym relationships to generate a second filtered set of CSMTCs;
    determining if the second filtered set of CSMTCs comprises more than one CSMTC; and
    in response to the second filtered set of CSMTCs comprising more than one CSMTC, applying a weighting to the second filtered set of CSMTCs based on the source reliability measure to generate a third filtered set of CSMTCs.

14. A code point resolver, comprising:
    a memory; and
    a processor that is configured to:
    receive, from the medical management system, medical text via a network interface, wherein a code point is a single standardized medical terminology code (SMTC) that corresponds to a medical concept contained within the medical text;
    apply rule-based logic to process the medical text to form a localized mapping of a text portion of the medical text to a plurality of candidate SMTCs (CSMTCs) that are related to at least one metathesaurus concept entity (MCE) in a metathesaurus and to determine the code point from the CSMTCs, wherein applying rule-based logic comprises:
       determining a fitness score with a fitness scorer of the rule-based logic for each of the CSMTCs using weightings that are based on a medical application intent, a hypernym and hyponym relationship, a source reliability measure, and codes determined by an industry acceptance rating; and
       determining the code point by selecting a best-fit SMTC having a highest fitness score of the CSMTCs; and transmit, via the network interface, to the medical management system, the code point.

15. The code point resolver of claim 14, wherein applying the rule-based logic further comprises:
parsing, with a natural language processor (NLP) of the rule-based logic, the medical text into one or more concepts that are each associated with one or more of the CSMTCs.

16. The code point resolver of claim 15, wherein applying the rule-based logic further comprises:
using the NLP to parse the medical text into medical text portions based on a mechanism selected from the group consisting of punctuation, keywords, and parts of language.

17. The code point resolver of claim 14, wherein the weightings are applied as a sequence of rules of the rule-based logic to the CSMTCs, wherein the sequence comprises:
applying a relevance determiner to the CSMTCs to generate a first filtered set of CSMTCs;
determining if the first filtered set of CSMTCs comprises more than one CSMTC;
in response to the first filtered set of CSMTCs comprising more than one CSMTC, applying a weighting to the first filtered set of CSMTCs based on the hypernym and hyponym relationships to generate a second filtered set of CSMTCs;
determining if the second filtered set of CSMTCs comprises more than one CSMTC; and
in response to the second filtered set of CSMTCs comprising more than one CSMTC, applying a weighting to the second filtered set of CSMTCs based on the source reliability measure to generate a third filtered set of CSMTCs.

18. A computer program product for a code point resolver, the computer program product comprising:
one or more computer readable storage media, and program instructions collectively stored on the one or more computer readable storage media, the program instructions comprising program instructions to:
receive, using a processor of a code point resolver, from the medical management system, medical text via a network interface, wherein a code point is a single standardized medical terminology code (SMTC) that corresponds to a medical concept contained within the medical text;
apply rule-based logic to process the medical text to form a localized mapping of a text portion of the medical text to a plurality of candidate SMTCs (CSMTCs) that are related to at least one metathesaurus concept entity (MCE) in a metathesaurus and to determine the code point from the CSMTCs, wherein applying rule-based logic comprises:
determining a fitness score with a fitness scorer of the rule-based logic for each of the CSMTCs using weightings that are based on a medical application intent, a hypernym and hyponym relationship, a source reliability measure, and codes determined by an industry acceptance rating; and
determining the code point by selecting a best-fit SMTC having a highest fitness score of the CSMTCs; and
transmit, via the network interface, to the medical management system, the code point.

19. The computer program product of claim 18, wherein determining the fitness score comprises using an additional element that is separate from the medical text and is selected from the group consisting of clinical notes and structured data.

20. The computer program product of claim 18, wherein the weightings are applied as a sequence of rules of the rule-based logic to the CSMTCs, wherein the sequence comprises:
applying a relevance determiner to the CSMTCs to generate a first filtered set of CSMTCs;
determining if the first filtered set of CSMTCs comprises more than one CSMTC;
in response to the first filtered set of CSMTCs comprising more than one CSMTC, applying a weighting to the first filtered set of CSMTCs based on the hypernym and hyponym relationships to generate a second filtered set of CSMTCs;
determining if the second filtered set of CSMTCs comprises more than one CSMTC; and
in response to the second filtered set of CSMTCs comprising more than one CSMTC, applying a weighting to the second filtered set of CSMTCs based on the source reliability measure to generate a third filtered set of CSMTCs.

* * * * *